United States Patent [19]

Zehner et al.

[11] Patent Number: 5,401,873
[45] Date of Patent: Mar. 28, 1995

[54] PREPARATION OF METHYL FORMATE

[75] Inventors: Peter Zehner, Ludwigshafen; Klaus Bittins, Frankenthal; Wilhelm Haarde, Gruenstadt; Ulrich Eiden, Frankenthal; Dietrich Wolff, Plankstadt; Manfred Herr, Wachenheim; Leopold Hupfer, Friedelsheim, all of Germany

[73] Assignee: BASF Aktiengesellschaft, Ludwigshafen, Germany

[21] Appl. No.: 208,823

[22] Filed: Mar. 11, 1994

[30] Foreign Application Priority Data

Mar. 25, 1993 [DE] Germany .......................... 43 09 731.6

[51] Int. Cl.⁶ .............................................. C07C 67/36
[52] U.S. Cl. ...................................... 560/232; 562/519
[58] Field of Search ................................ 560/232, 239

[56] References Cited

U.S. PATENT DOCUMENTS

| | | | |
|---|---|---|---|
| 2,160,064 | 5/1939 | Eversole | 560/239 |
| 4,149,009 | 4/1979 | Yonecka et al. | 560/239 |
| 4,216,339 | 8/1980 | Couteau et al. | 560/232 |
| 4,661,624 | 4/1987 | Chang et al. | 560/232 |
| 5,194,675 | 3/1993 | Joerg et al. | 560/239 |

FOREIGN PATENT DOCUMENTS 2710726 9/1977 Germany .

OTHER PUBLICATIONS

Japanese Abst. 87/22744 (1987).

Primary Examiner—Arthur C. Prescott
Attorney, Agent, or Firm—Keil & Weinkauf

[57] ABSTRACT

Preparation of methyl formate by the reaction of carbon monoxide and methanol under conditions of elevated pressure and temperature in the presence of an alkali metal methylate, in which A) the starting materials are mixed in a mixing zone, are allowed to react partially, and the reaction solution is saturated with CO and B) the reaction is allowed to reach completion in one or more secondary reaction zones without the addition of further starting materials.

7 Claims, 1 Drawing Sheet

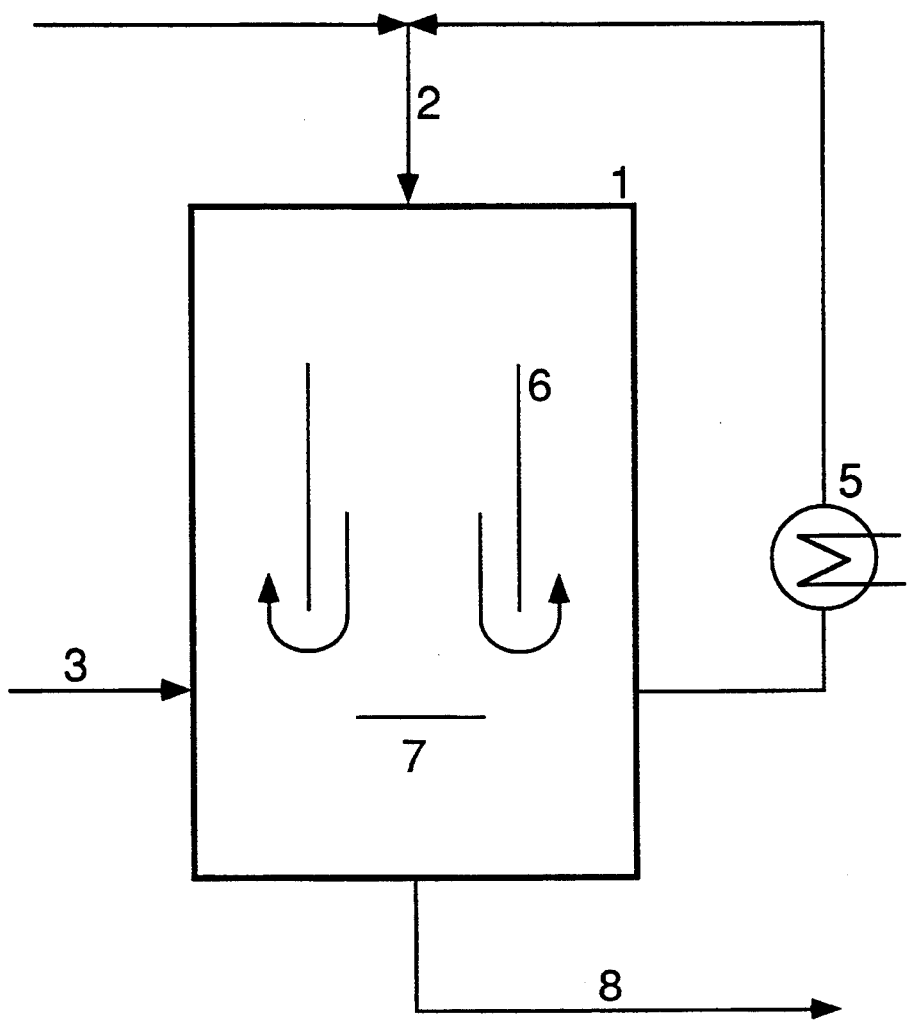

PREPARATION OF METHYL FORMATE

The present invention relates to a process for the preparation of methyl formate from carbon monoxide and methanol under conditions of elevated pressure and temperature in the presence of an alkali metal methylate.

This method of preparing methyl formate has been known on a theoretical basis for many years. However, large-scale production involves a number of problems.

U.S. Pat. No. 4,661,624 describes a process for the preparation of methyl formate from CO and methanol in the presence of sodium methylate acting as catalyst. In order to achieve a high reaction rate, this process is operated at a high catalyst concentration and at low conversion rates. As a result, unconverted methanol must be recycled following removal of the product by distillation, in order to render the process economical, and a major portion of the carbon monoxide used is not utilized or must be recycled in an energy-consuming manner following compression. To improve the CO efficiency, in a preferred embodiment, two reaction zones can be connected to form a cascade, both of which are charged with recycled methanol and through which the GO gas is passed successively. However, the conversion of CO remains below 90%.

JP-A 87/22744 relates to a process for the preparation of methyl formate from CO and methanol in an annular reactor. The vigorously blended starting materials are pumped through the reactor. According to the teaching of this reference a mixture of methyl formate, methanol and CO dispersed therein needs to be reprocessed, so that if the gas is not adequately recycled the losses of CO are relatively high.

DE-A 2,710,726 teaches a process for the preparation of methyl formate, in which CO is sucked by a recycled stream of the reaction mixture into the vigorously agitated reaction zone. Quantitative CO conversion is unattainable in this process, however, since at least that amount of CO is removed from the circuit, together with the product stream, which is dissolved therein in a concentration determined by the CO partial pressure.

It is an object of the present invention to provide a process which makes it possible to prepare methyl formate at a high CO conversion rate and a correspondingly low CO recycle rate.

Accordingly, we have found a process for the preparation of methyl formate from carbon monoxide (CO) and methanol under conditions of elevated pressure and temperature in the presence of an alkali metal methylate, wherein A) the starting materials are mixed in a mixing zone, are allowed to react partially, and the reaction solution is saturated with CO and B) the reaction is allowed to reach completion in one or more secondary reaction zones without the addition of further starting materials.

The overall reaction can be represented in the following manner

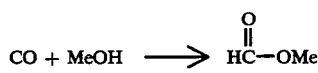

Me=methyl

The process of the invention can be carried out using CO optionally containing an inert gas such as nitrogen, and it is preferred to use a gas having a CO content of more than 93 vol %. Generally speaking, the water content of the gas is less than 100 ppm, to prevent decomposition of the catalyst. As catalyst there are used alkali metal methylates, of which sodium methylate is preferred. CO, methanol and the catalyst dissolved in the methanol are usually intermixed in the mixing zone. An advantageous way of achieving this end is to disperse the gas phase in the liquid phase as well as possible so as to achieve a high reaction rate.

In the mixing zone a high CO partial pressure leads to a high reaction rate. During the reaction overall pressures ranging from 10 to 300 bar can be used, preferably from 20 to 150 bar and more preferably from 40 to 100 bar.

The temperature can be from 60° to 120° C. and preferably from 70° to 90° C. The catalyst concentration is generally from 0.1 to 3wt % and preferably from 0.4 to 1.5 wt %, based on methanol used. The molar ratios of methanol and CO may be from 2:1 to 8:1, preferably from 3:1 to 5.5:1 and more preferably from 3.5:1 to 4.5:1. An excess of methanol promotes a high CO conversion, on the one hand, but it causes, on the other hand, the catalyst, which is insoluble in pure methyl formate, to remain in solution. In the mixing zone the CO conversion can be controlled by regulating the residence time, and good results have been obtained using conversion rates of from 85 to 95% of the CO used. During the mixing phase, the reaction mixture becomes saturated with unreacted CO.

The resulting reaction mixture of methyl formate, methanol, dissolved catalyst and dissolved CO is passed, according to the invention, into one or more secondary reaction zones, and no further starting compounds are added. Undissolved CO remains in the mixing zone and the dissolved CO reacts to form the product. Using an adequate residence time the reaction thus continues until a state of equilibrium is reached.

This secondary reaction can be effected, in practice, e.g., by passing the reaction mixture into one or more in-line boilers, in which different concentrations prevail. Another possibility is to allow the reaction to proceed to completion in a tube.

BRIEF DESCRIPTION OF THE DRAWINGS

A particularly preferred embodiment of the process of the invention is diagrammatically illustrated in the accompanying drawing.

Methanol and catalyst are fed to a reactor 1 via a feed line 2; CO is passed through a feed line 3 and gas distribution means to the reactor 1. The reaction mixture is circulated through an external circuit 4. During this operation the heat of reaction is removed by a heat exchanger 5. In the reactor 1 guides 6 and a baffle plate 7 ensure that the reaction mixture in the mixing zone is forced to circulate internally, which causes the gas and liquid to be intimately intermixed. The secondary reaction zone is disposed below the mixing zone, so that the reaction solution falls under the action of gravity. Undissolved CO can escape upwardly into the mixing zone. At the bottom of reactor 1 the fully reacted reaction solution can be withdrawn via line 8.

Purification of the reaction solution obtained by the method of the invention is carried out in known manner. Following pressure-release and removal of residual gas it is usual to carry out distillation of the liquid components with possible feedback of the methanol thus obtained. Methyl formate can then be hydrolyzed to formic acid in known manner.

The process of the invention makes it possible to convert CO dissolved in the reaction mixture to such an extent that recycling thereof to the reaction is no longer worthwhile or becomes unnecessary. The process has the added advantage of achieving a high space-time yield using a reactor of small dimensions.

EXAMPLE

In a continuous reactor as shown in the accompanying drawing and operated under an overall pressure of 57 bar and at a temperature of 80° C., methanol and pure CO were mixed in a molar ratio of 3.6:1 in the presence of 1 wt % of sodium methylate, based on methanol. With the residence time set at 45 min, the content of methyl formate was 40 percent by weight. The CO conversion was 92%. As the result of a secondary reaction phase lasting 2 min, the CO conversion rose to 95.5% whilst the loss of CO was reduced by almost fifty percent due to CO dissolved in the reaction mixture.

We claim:

1. A process for the preparation of methyl formate by the reaction of carbon monoxide and methanol under conditions of elevated pressure and temperature in the presence of an alkali metal methylate, wherein
   A) the starting materials are mixed in a mixing zone, are allowed to react partially, and the reaction solution is saturated with CO and
   B) the reaction is allowed to reach completion in one or more secondary reaction zones without the addition of further starting materials.
2. A process as defined in claim 1, wherein the pressure used ranges from 40 to 100 bar.
3. A process as defined in claim 1, wherein the temperature used ranges from 60° to 100° C.
4. A process as defined in claim 2, wherein the temperature used ranges from 60° to 100° C.
5. A process as defined in claim 1, wherein sodium methylate is used as catalyst.
6. A process as defined in claim 2, wherein sodium methylate is used as catalyst.
7. A process as defined in claim 1, wherein the catalyst concentration in the mixing zone is from 0.4 to 1.5 wt %, based on methanol used.

* * * * *